United States Patent
Jenkinson et al.

(10) Patent No.: US 6,766,762 B2
(45) Date of Patent: Jul. 27, 2004

(54) INDICATOR DEVICE FOR SOIL

(75) Inventors: Byron J. Jenkinson, West Lafayette, IN (US); Donald P. Franzmeier, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/264,278

(22) Filed: Oct. 3, 2002

(65) Prior Publication Data

US 2003/0101922 A1 Jun. 5, 2003

Related U.S. Application Data

(60) Provisional application No. 60/327,422, filed on Oct. 5, 2001.

(51) Int. Cl.[7] .............................................. G01D 21/00
(52) U.S. Cl. ..................... 116/206; 73/290 R
(58) Field of Search ................. 116/206, 207, 116/216; 73/73, 290 R; 374/160, 162; 47/48.5, 58.1 R, 58.1 C; 428/472.2, 702; 106/286.1, 286.3

(56) References Cited

U.S. PATENT DOCUMENTS

| | | | | |
|---|---|---|---|---|
| 2,787,238 A | * | 4/1957 | Luce ........................... | 116/206 |
| 3,246,758 A | * | 4/1966 | Wagner ....................... | 210/94 |
| 3,702,755 A | * | 11/1972 | Palmer ........................ | 422/55 |
| 3,881,873 A | * | 5/1975 | Klowden ..................... | 422/56 |
| 4,184,445 A | * | 1/1980 | Burrows ..................... | 116/206 |
| 4,201,080 A | * | 5/1980 | Slepak et al. ................. | 73/73 |
| 4,382,380 A | * | 5/1983 | Martin ......................... | 73/73 |
| 4,846,572 A | * | 7/1989 | Alasaarela ................... | 356/136 |
| 5,048,334 A | * | 9/1991 | Hampton et al. ......... | 73/290 R |
| 5,095,844 A | * | 3/1992 | Alexander ................... | 116/206 |
| 5,694,806 A | * | 12/1997 | Martin et al. ................. | 73/73 |
| 6,058,647 A | * | 5/2000 | Emalfarb ................. | 47/1.01 R |
| 6,460,480 B1 | * | 10/2002 | Schlosser et al. ........... | 116/206 |
| 2002/0110509 A1 | * | 8/2002 | Lundy ........................ | 423/143 |

* cited by examiner

Primary Examiner—Diego Gutierrez
Assistant Examiner—Amy R Cohen

(57) ABSTRACT

A soil indicator device is adapted to be disposed in the soil and has a substrate with an indicator coating thereon that is removable from the substrate when the indicator device is exposed to anaerobic soil conditions so that the indicator device changes color at least to some extent from that of the original coating.

18 Claims, 1 Drawing Sheet

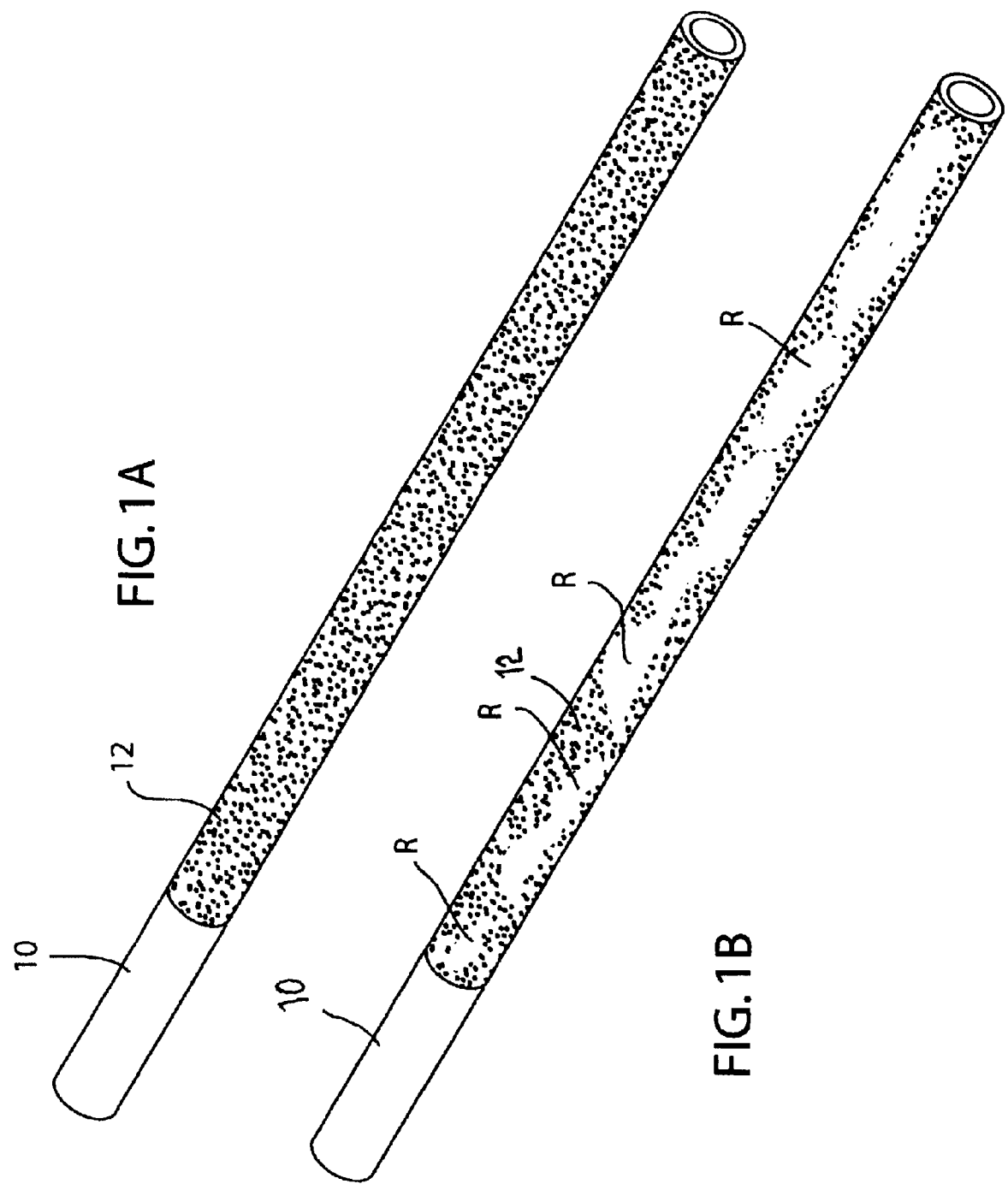

INDICATOR DEVICE FOR SOIL

This application claims the benefits of provisional application Serial No. 60/327,422 filed Oct. 5, 2001.

CONTRACTUAL ORIGIN OF THE INVENTION

This invention was made under Grant: Soil Sampling, Agronomy Account No. 596 1150-0041 50051 of the United States Department Of Agriculture-Natural Resources Conservation Service, 6013 Lakeside Boulevard, Indianapolis, Ind.

FIELD OF THE INVENTION

The invention relates to an indicator device and method for determining whether a soil is hydric.

BACKGROUND OF THE INVENTION

Natural wetlands collect and purify surface water before it reaches the streams and aquifers that provide our drinking water. They also serve as habitats for many birds and animals, and they provide areas for recreation. We have drained or developed most of the wetlands in the U.S. In recent years, however, Americans decided, through congressional action, to preserve our remaining wetlands. Because wetland cannot be drained or developed, there is much interest in whether or not a specific tract of land qualifies as a wetland. This device will help wetland delineators make that decision.

In 1987 the Army Corps. Of Engineers published the Wetland Delineation Manual in response to federal legislation mandating the protection of wetlands. Additional federal publications for identifying and delineating wetlands 59 FR 35680, Jul. 13, 1994, and 60 Fr 10349, Feb. 24, 1995 were published. According to the documents, wetlands cannot be drained or destroyed by development under penalty and or special mitigation requirements. Jurisdictional wetlands have three essential requirements: hydric soils, hydrophytic vegetation, and wetland hydrology. By definition, hydric soils are those that are saturated, flooded, or ponded long enough during the growing season to develop anaerobic conditions in the upper part. That is, hydric soils have a water table at or near surface for a time long enough during the growing season to become anaerobic. In saturated soils anaerobic microorganisms use compounds such as nitrate, manganese oxides and/or iron oxides as an electron acceptor instead of oxygen in respiration processes. A byproduct of this microbial activity is the increased mobility of Mn and Fe in the soil solution. The saturated conditions of the hydrology factor, the soil oxygen deficiency of the vegetation factor, and the anaerobic conditions of the soil factor are all related (Franzmeier, D. P., E. J. Kladivko, and B J Jenkinson. 2001. Drainage and Wet Soil Management. Purdue University Cooperative Extension Service).

An object of the invention is to provide an indicator device and method for determining whether a soil is hydric.

SUMMARY OF THE INVENTION

The present invention provides an indicator device that is adapted to be disposed in the soil and that exhibits a change in color when exposed to anaerobic conditions over time. In an illustrative embodiment of the invention, the indicator device comprises a substrate having an indicator coating thereon that is at least partially removable from the substrate at one or more regions of the coating when the indicator device is exposed in the soil to anaerobic conditions over time so that indicator device changes color at the one or more regions. The indicator coating is not removed when the device is exposed to aerobic soil conditions. The indicator device is removed from the soil for visual inspection to determine its color change.

In an illustrative embodiment of the invention, the substrate comprises a PVC (polyvinyl chloride) tube or sheet coated with a coating of iron or other metal oxide, such as for example, ferrihydrite, such that, when the indicator device is installed in a soil and exposed to sustained anaerobic conditions, the oxide coating will be removed at least partially through its thickness at one or more regions and ultimately may expose the underlying white PVC substrate, thereby providing a visual indicator in the field that reducing soil conditions were present.

DESCRIPTION OF THE DRAWINGS

FIG. 1A is an elevational view of an indicator device before placement in the soil.

FIG. 1B is a representation of an indicator device of the invention after placement in the soil under anaerobic conditions and upon removal from the soil for visual inspection.

DESCRIPTION OF THE INVENTION

An indicator device pursuant to an embodiment of the invention comprises a substrate 10 which preferably comprises a PVC (polyvinyl chloride) tube, rod or sheet, although other materials can be used for the substrate. The substrate is coated with an indicator coating 12 thereon, FIG. 1A, that is at least partially removed through its thickness at one or more coating regions R, FIG. 1B, when the indicator device is exposed in the soil to anaerobic conditions over time. The indicator device thereby changes color at the one or more regions R from the color of the original indicator coating. The visual indicator coating is not removed when the device is exposed to aerobic soil conditions over time. An indicator coating useful in practice of the invention comprises a metal oxide, such as for example an iron oxide coating comprising ferrihydrite, goethite, lepidocrocite, and/or hematite, a manganese oxide such as for example, birnessite, and other metal oxides and compounds that will be removed from the substrate by exposure to anaerobic soil conditions over time to cause a change in color of the indicator device. An indicator coating thickness can be about 0.001 inch or less, although other coating thicknesses can be used.

An illustrative substrate comprises white PVC tubing, rod, or sheet having a variegated reddish brown and yellow ferrihydrite coating 12 thereon. Ferrihydrite is an iron-containing mineral that is common in many soils and is relatively insoluble in soil solutions that have free access to oxygen. When exposed to sustained anaerobic soil conditions, the thickness of the ferrihydrite coating is dissolved at least partially at one or more coating regions in the soil solution, thereby providing a visual indication that in the field reducing hydric soil conditions were present. Each ferrihydrite coated PVC tube is inserted in a hole in the soil that is slightly smaller in diameter than the tube diameter. In a few weeks or months, the tubes are pulled out and examined. In freely drained aerobic soils the ferrihydrite coating is not dissolved, even though much water leaches through the soil and it is saturated for short periods of time, and the rods retain their reddish brown color. If however, the soil becomes saturated with water for a longer time, the soil solution becomes anaerobic (depleted of oxygen), iron is reduced ($Fe^3+ \rightarrow Fe^2+$), ferrihydrite dissolves, and portions or regions R or all of the indicator device become(s) yellowish from partial dissolution of the coating thickness or possibly become(s) white (the color of the PVC tube 10) when there is complete removal of the coating to expose the white PVC tube. The whiter the indicator device, the more the reduction that has occurred in the soil. Qualitative evaluations can be made by comparing the colors on the indicator device surface with the color of those that were never installed in the soil and with a standard color chart. The surface area of altered ferrihydrite can be estimated or measured. Quantitative measurements can be made by photographing the indicator devices and analyzing the color and the surface area using computer software. Thus, when the ferrihydrite coated tubes are installed in anaerobic soils that are saturated and reduced for a short time, some of the coating is dissolved as a result of microbial activity, thereby providing a visual indicator in the field that reducing conditions were present.

The following Example is offered for purposes of illustration and not limitation.

EXAMPLE

An indicator device is made from schedule 40 polyvinyl chloride (PVC) plastic. The PVC tubing is ½ inch inside diameter PVC tubing. The sheet form of PVC can also be used. The outside surface dimension of the tube is ⅞ inch (diameter). The length of the tube is 23 ⅝ inches (length).

The oxide coating is made by dissolving 40 g ferric chloride salt ($FeCl_3$) in 500 ml deionized water and adjusting pH of the resulting solution as described below (also described in Schwertmann, U., H. Fechter, R. M. Taylor, and H. Stanjek. 1993. A Lecture and Demonstration for Students relating to iron oxide formation. Proceedings of the International Clay Conference. CSIRO Publishing, Melbourne Australia, the teachings of which are incorporated herein by reference). The pH of the resulting solution is initially raised with the addition of about 330 ml of potassium hydroxide (1 molar solution) while stirring. More of the potassium hydroxide solution is added to bring the solution pH to approximately pH 7 to 8. The pH change causes ferrihydrite to precipitate in the solution. Next, the suspension of ferrihydrite is centrifuged to accrete precipitate to the bottom of the container, clear solution is decanted, and the container is refilled with about 600 ml of deionized water. The remaining salts (e.g. potassium chloride) are removed from solution using dialysis (osmosis) techniques using SPECTRA/POR molecularporous membrane tubing available from Fisher Scientific Co. Silver nitrate is used to test for presence of salt. After the salts are removed, the wet precipitate is transferred to a sealed vessel and stored wet. The time of the salt/precipitate separation can vary with size of batch. In the wet state ferrihydrite is the dominant species; however some ferrihydrite is transformed geothite when wet and to hematite when dried.

Construction of Oxide Coated Tubes:

1. Tubes are cut to a length of 23 ⅝ inches (60 cm).
2. Each tube is then cleaned with acetone.
3. The tube is then fastened to a lath type device or a drill (both ends must be stabilized) and rotated (about 75 rpm). As the tube is rotated, the following operations are done:

a. The bottom 20 inches (50 cm) of the tube is sanded with 100 grit sandpaper and then wiped clean.
   b. The wet ferrihydrite precipitate is applied to the surface with a sponge brush applicator by moving the applicator along the sanded surface. The resultant coating should look smooth and have a variegated pattern of brown and yellow color.
   c. While the tube is still rotating, a high temperature heat gun applies a stream of hot air (>200° F.), along the tube surface and then back quickly drying the coating. When the coating is dried to the touch the tube is removed from the lath and allowed to cure in air for 24 hours.
   d. A second coat is then applied (steps b and c), and allowed to air cure for another 24 hours. A second coat lowers the value of the color and increases the chroma of the coating color. The second coating is allowed to cure for 24 hours. Area of oxide coating was 6.91 cm by 50 cm. Total coating thickness was about 0.001 inch.

Ferrihydrite coated tubes were placed in nine soils in Indiana in the winter. Only two soils were saturated with water close to the surface. The coated tubes installed at these sites had part of the coating removed. The coating on the tubes in unsaturated soils was not affected. The test was repeated the next winter and spring at the same sites and additional ferrihydrite coated tubes were installed at other sites in Indiana, Minnesota and North Dakota. The iron oxide coatings were removed from all tubes installed in periodically saturated soils.

Although the invention has been described with respect to certain embodiments thereof, those skilled in the art will appreciate that the invention is not so limited and various changes, modifications and the like can be made therein without departing from the spirit and scope of the invention as set forth in the appended claims.

We claim:

1. A soil indicator device for indicating if a soil is hydric, said device being adapted to be disposed in the soil, comprising a substrate having a first color and an indicator coating thereon that has a second color different from said first color and that is removed at least partially at one or more regions thereof when the indicator device is exposed to anaerobic conditions over time, said indicator device changing color at said one or more regions as a result of at least partial removal of said coating, wherein said color change indicates that the soil is hydric.

2. The device of claim 1 wherein said indicator coating comprises a metal oxide.

3. The device of claim 2 wherein said metal oxide comprises iron oxide.

4. The device of claim 3 wherein said iron oxide comprises ferrihydrite.

5. The device of claim 1 wherein said substrate comprises an elongated tube or rod having said indicator coating thereon.

6. The device of claim 1 wherein said substrate comprises a sheet having said indicator coating thereon.

7. The device of claim 1 wherein said substrate is white in color.

8. The device of claim 1 wherein said indicator coating has a thickness of about 0.001 inch or less.

9. A method of testing a soil to indicate if the soil is hydric, comprising placing in the soil an indicator device comprising a substrate having a first color and an indicator coating thereon that has a second color different from said first color and that is at least partially removable at one or more regions thereof when the indicator device is exposed to anaerobic soil conditions over time so that the indicator device changes color at said one or more regions as a result of at least partial removal of said coating, and removing the indicator device from the soil for inspection, wherein said color change indicates that the soil is hydric.

10. The method of claim 9 wherein said indicator coating comprises a metal oxide.

11. The method of claim 10 wherein said metal oxide comprises iron oxide.

12. The method of claim 11 wherein said iron oxide comprises ferrihydrite.

13. The method of claim 9 wherein said substrate comprises an elongated tube or rod having said indicator coating thereon.

14. The method of claim 9 wherein said substrate comprises a sheet having said indicator coating thereon.

15. The method of claim 9 wherein said substrate is white in color.

16. The method of claim 9 wherein said indicator coating has a thickness of about 0.001 inch or less.

17. The method of claim 9 including placing said indicator device in a preformed hole in the soil wherein said hole is smaller in diameter than a diameter of said indicator device.

18. The method of claim 9 including placing said indicator device in the soil for a period of time of several weeks or more.

* * * * *